United States Patent [19]

Solman et al.

[11] Patent Number: 4,723,511
[45] Date of Patent: Feb. 9, 1988

[54] CONTINUOUS MONITORING OF WATER QUALITY

[75] Inventors: Arthur J. Solman, Monks Risborough; Graham P. Evans, Marlow, both of England

[73] Assignee: Water Research Centre, Buckinghamshire, England

[21] Appl. No.: 721,436

[22] Filed: Apr. 8, 1985

[30] Foreign Application Priority Data

Apr. 13, 1984 [GB] United Kingdom ............... 8409646

[51] Int. Cl.$^4$ ........................................... A01K 61/00
[52] U.S. Cl. ...................................................... 119/3
[58] Field of Search ........................................... 119/3

[56] References Cited

U.S. PATENT DOCUMENTS

| 4,580,525 | 4/1986 | Marzluf | 119/3 |
| 4,593,648 | 6/1986 | Marzluf | 119/3 |
| 4,626,992 | 12/1986 | Greaves | 119/3 |

FOREIGN PATENT DOCUMENTS

| 789079 | 12/1980 | U.S.S.R. | 119/3 |
| 1109102 | 8/1984 | U.S.S.R. | 119/3 |

OTHER PUBLICATIONS van der Schalie, "Utilization of Aquatic Organisms for Continuously Monitoring the Toxicity of Industrial Waste Effluents", *Technical Defense Information Center,* paper 22 (1981).

Poels, "An Automatic System for Rapid Detection of Acute High Concentrations of Toxic Substances in Surface Water Using Trout", ASTM STP 607, pp. 85–95 (1977).

Cairns, Jr. and Gruber, "A Comparison of Methods and Instrumentation of Biological Early Warning Systems", *Water Resourses Bulletin,* vol. 16, No. 2, pp. 261–266 (Apr. 1980).

Morgan, "Biomonitoring with Fish: An Aid to Industrial Effluent and Surface Water Quality Control", *Prog. Water Tech.,* vol. 9, pp. 703–711, Pergamon Press (1977).

*Primary Examiner*—Robert Peshock
*Assistant Examiner*—Cary E. Stone
*Attorney, Agent, or Firm*—Watson, Cole, Grindle & Watson

[57] ABSTRACT

A supply of water is continuously monitored to ensure purtiy by dividing the supply into a number of parallel streams and flowing each through a fish tank containing a fish (or other aquatic animal), the health of each fish being monitored by electrodes in each respective tank. The fish tanks are located together in a main tank and the water supply is drawn from a header tank via pipework, the tank being fed from supply. The apparatus includes an electronic system to monitor the activity of the fish.

12 Claims, 12 Drawing Figures

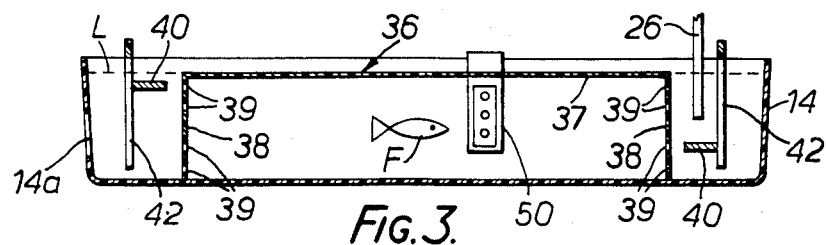
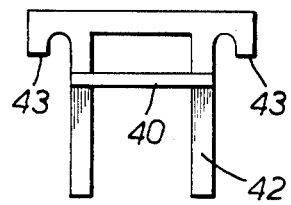
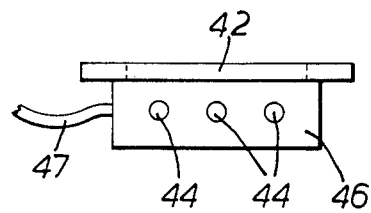
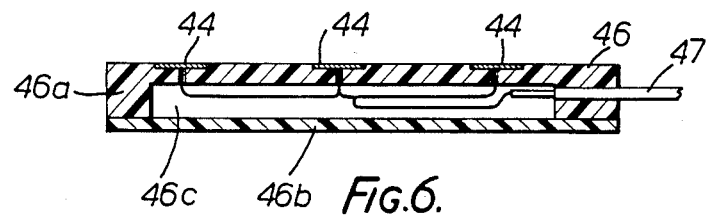

CONTINUOUS MONITORING OF WATER QUALITY

This invention relates to a continuous monitoring of water using aquatic animals, usually fish, to protect against and give warning of noxious concentrations of substances in the water.

It is desirable to be able to monitor water continuously so as to be able to take action as early as possible if the water becomes contaminated or otherwise impaired in quality. There have been proposals to monitor water quality by passing the water through a tank containing fish and to monitor small electrical potentials which are generated in accordance with normal fish physiology, such as respiration and heart beat: such physiological characteristics of the fish change when the fish are exposed to water which is contaminated or otherwise poor in quality.

We have now devised an improved water monitoring apparatus which is of improved reliability over prior proposals and is sensitive in operation and of relatively simple construction.

In accordance with this invention, there is provided apparatus for continuously monitoring a flowing water supply, which comprises a main tank having a plurality of discrete regions therein each for an aquatic animal, means for dividing the flowing water supply into a series of parallel flowing streams to provide one stream through each said region and therefrom into said main tank, each region having therein a pair of electrodes spaced apart; and an electronic system arranged (in use of the apparatus) to monitor the activity of aquatic animals in the individual regions from signals from the respective electrodes.

The invention also provides a method of continuously monitoring a flowing water supply, which comprises dividing the supply into a series of parallel flowing streams, and feeding each stream through a respective discrete region of a main water tank comprising a plurality of said regions, each said region containing an aquatic animal and having a pair of electrodes spaced apart therein, and using an electronic system to monitor the signals from the electrodes in the individual regions.

In accordance with the present invention, the preferred aquatic animals are fish, especially rainbow trout. Other aquatic animals can be used provided that they emit appropriate electrical signals which enable their condition to be monitored. Hereinafter, the invention will be described with reference to the use of fish, it being understood that other aquatic animals (e.g. crayfish or yabbie) can be used instead.

It is a feature of the present invention that the water supply to be monitored is divided into streams so that each fish experiences a sample of the same water as the other fish. Thus, each discrete region of the main tank will normally house one fish only, and each region will receive one stream of water, so that normally at any moment each fish in its own discrete region is experiencing the "same" water as each of the others. By "same" we mean water derived from the same unit volume of supply. It is also important that, so far as reasonably possible, each fish should be in the same size and shape of region as the others, and that the water flow rate through each region should be the same. Thus, each fish should be in the same environment as each of the others. If the water supply becomes polluted, all the fish will experience the pollutant roughly simultaneously.

It is possible for the flow of a sample stream to any one or more of the regions of the tank to be delayed (for example by use of a longer flow path), but in such cases the electronic system monitoring the electrode signals will be pre-set to allow for the delay, so that it is only those signals from the fish as they experience the "same" water which are utilised for monitoring.

The sample streams are flowed to their respective discrete regions in the main tank, and after flow therethrough exit the regions and enter the main tank area (not occupied by said regions). Preferably, the water outlet from the main tank is by way of a weir, since this automatically maintains a constant water level in the main tank. Preferably, the water flowing over the weir is received in a pot or like vessel with a tapering (conical) lower portion to assist in preventing any break in flow of the water downstream thereof.

The discrete regions in the main tank can be defined in a variety of ways, e.g. using electrically insulating baffles or the like. However, we prefer to use individual fish tanks to define the regions, each such tank normally constituting one region and containing a fish therein. Normally, the tanks are elongate and each receives its respective water stream at one end of the tank and has an outlet at the other end. Each fish tank is placed in the main tank and water exiting the fish tanks passes into the main tank.

We have found that in the arrangements of the invention as described above, there can be cross-talk between the signals generated by fish in adjacent tanks. According to a highly preferred feature of the invention, we have found that this cross-talk can be substantially reduced, e.g. by a factor of 10, by slightly increasing the electrical resistance between the water in the fish tank and the water in the main tank (i.e. not in any fish tank). A preferred way of providing this additional electrical resistance comprises providing a tube at the outlet from each fish tank (extending upstream or downstream of the tank wall), so that all the water exiting from the fish tank must pass through the tube. The tube is of such a length and bore to provide the required increase in resistance (e.g. a few ohms) without significantly affecting the water-flow rate. By effecting such a substantial reduction in cross-talk, discrimination is very much improved resulting in a greater sensitivity for the apparatus and method.

In one embodiment of the invention to be described herein, the main tank is open-top and is mounted at table-height so that the fish tanks can easily be removed from the main tank for cleaning. Also, the fish tanks are preferably open-top and the electrodes are arranged to be easily locatable in the fish tanks. A lid can be provided for each fish tank, or to extend over all the fish tanks.

In accordance with a preferred feature of this invention, we use electrodes comprising at least one sintered element of silver and silver chloride, encapsulated in insulating material but with a major face of the sintered element exposed at a surface of the electrode. These electrodes are novel and constitute one aspect of this invention. In one embodiment, three sintered elements, in the form of discs, are spaced-apart in line and encapsulated in a flat member of plastics material with one side of each disc coplanar with one side of this flat member. The other sides of the discs are provided with pigtails (also encapsulated by the plastics material)

which are connected together and to a low noise cable leading to an amplifier.

In the embodiment to be described, the apparatus further comprises a micro computer system for monitoring and analysing the electrical output from the pair of electrodes in each fish tank.

Embodiments of this invention will now be described, by way of example only, with reference to the accompanying drawings, in which:

FIG. 3 is a longitudinal section through one of the fish tanks;

FIG. 4 is an elevation of one of the pair of electrode carriers;

FIG. 5 is a plan view of the electrode carrier of FIG. 4, showing the electrode itself;

FIG. 6 is a longitudinal sectional view of an electrode of the invention;

FIG. 7 is a longitudinal sectional schematic view of the reference electrode of FIG. 3;

Figure 1:
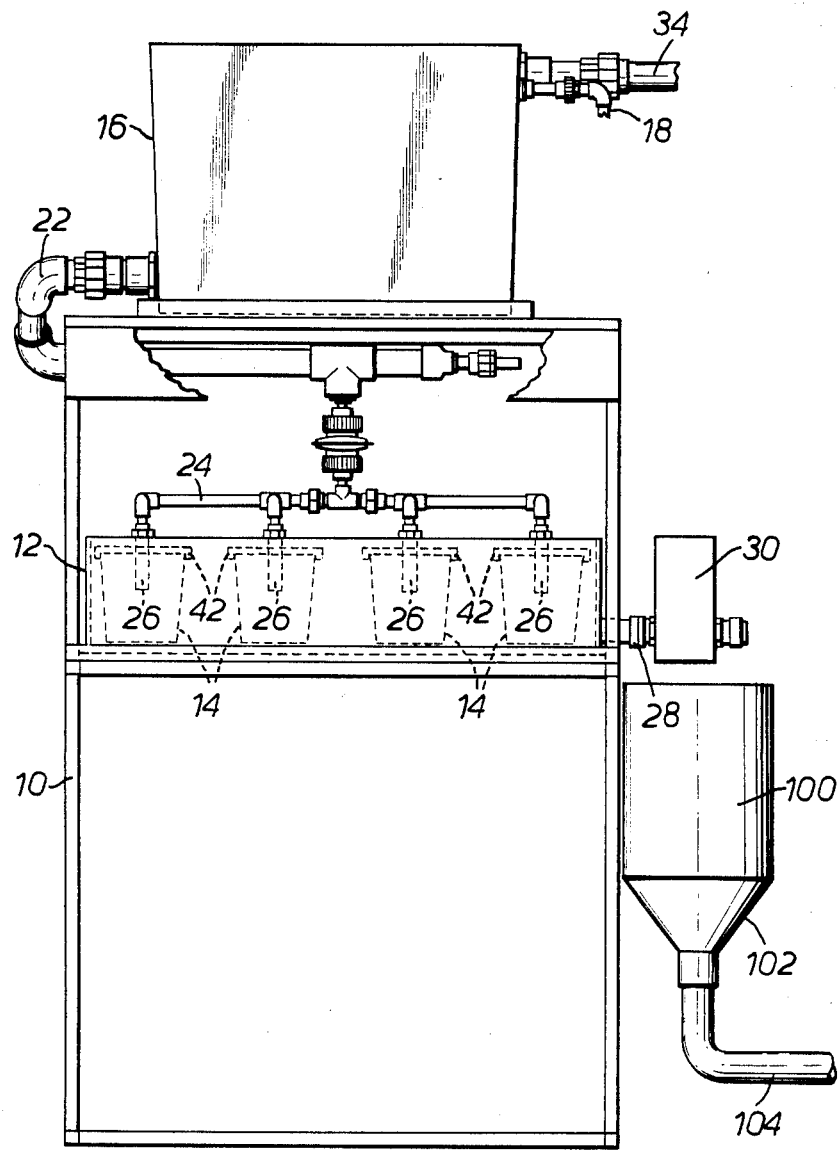
FIG. 1 is a front view of an arrangement of tanks in an embodiment of water monitoring apparatus.
Figure 2:
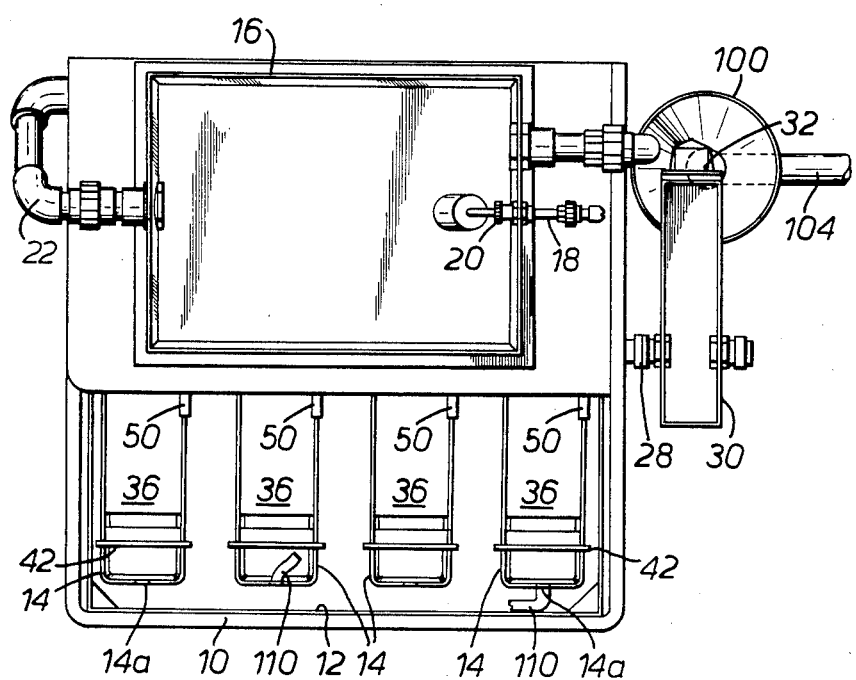
FIG. 2 is a plan view of the tank arrangement of FIG. 1.
Figure 8:
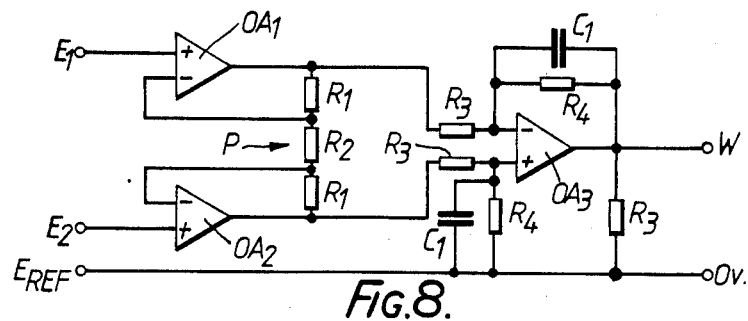
FIG. 8 is a circuit diagram of an input stage of an amplifier for the analogue signals detected by the pair of electrodes.

Referring to FIGS. 1 and 2, there is shown the arrangement of tanks of a water monitoring apparatus in accordance with this invention. A frame structure 10 supports an open-top, main tank 12 at table-top or waist-height. A plurality of open-top, elongate fish tanks 14 (for example four in number) are removably placed side-by-side within the main tank 12. The frame structure 10 supports a header tank 16 above the main tank 12 and this header tank receives water, which is to be monitored, through an inlet pipe 18 provided with a float controlled valve 20. An outlet pipe 22 runs from adjacent the bottom of the header tank to a horizontal manifold pipe 24 disposed above and transversely of the main tank 12. Vertical pipes 26 run downwards from the manifold pipe 24 and into the respective fish tanks, terminating adjacent one end of each fish tank and either below the normal level of water therein or above it in which case preferably they are formed with an internal conical taper towards their outlet ends, so as to provide for a steady jet of water and therefore a constant electrical impedance to earth.

The opposite end of each fish tank is formed with an aperture 14a, below the normal level of water in the main tank, for water to flow from the individual fish tanks and into the main tank. One wall of the main tank is formed with an aperture communicating with an outlet pipe 28 which passes to an open-top rectangular vessel 30, adjacent one end thereof. An opposite end of vessel 30 is cut-away from its top edge to form a weir 32: the vessel is mounted for limited rotation about the axis of pipe 28 so as to adjust the height of the weir 32 and accordingly the level of water in the vessel 30 and correspondingly in the main tank 12 and the individual fish tanks 14. Below the weir is collecting pot 100 which has a tapering base portion 102 connecting to pipe 104 to carry the water away. The tapering portion 102 serves to reduce the risk of discontinuities in the water downstream thereof.

As illustrated in FIG. 2, two of the tanks 14 have, at their outlets 14a, a short length of tubing 110. In one case (the right-hand tank of FIG. 2), the tubing extends downstream from outlet 14a, whereas in the other example, the tubing extends upstream from the outlet, i.e. it extends into the respective fish tank. In both cases, all the water leaving the respective fish tank through outlet 14a has to flow through tubing 110. This tubing is of a length and bore to increase the electrical resistance between the fish tank water and the main tank water without hindering the flow of water out of the tank. Only two of the illustrated fish tanks have outlet tubing 110 but, in practice, all the tanks will normally have it, extending downstream from the outlet 14a.

Thus in use, the water to be monitored is passed into the header tank 16 and is then continuously distributed to the individual fish tanks through the pipes 22, 24 and 26. The water then passes to the opposite end of each fish tank, through its aperture 14a (and in some cases, tubing 110) and into the main tank 12, from which it continues to pass through the outlet pipe 28 to the vessel 30, over the weir 32 and into the open top of pot 100 to pipe 104. The header tank 16 is further provided with an overflow pipe 34 which can lead (not shown) to this pipe 104.

Referring to FIG. 3, each fish tank 14 comprises a trough moulded of plastics material and is provided with a removable baffle member 36 of transparent plastics material. This baffle member comprises an elongate top portion 37 and two depending end wall portions 38, by which the baffle member stands on the bottom of the fish tank, and which are formed with a series of apertures 39 for the through-flow of water. One fish F is to be confined between the end wall portions 38. Beyond the opposite ends of the baffle member, a pair of electrodes 40 are removably disposed, below the water level L, each electrode being mounted on a flat plastics carrier member 42 provided at its opposite vertical edges with hooks 43 (FIG. 4) for resting upon the side edges of the fish tank.

Referring to FIGS. 5 and 6, each electrode comprises three sintered discs 44 of silver and silver-chloride encapsulated by a flat member 46 of PVC so as to space-apart in a line and have their front surfaces co-planar with a surface of member 46. On its rear surface each disc 44 is provided with a pigtail, also encapsulated by the member 46 but joined together and to an insulated and screened conductor 47 which leads to the electronic monitoring system. As shown in FIG. 6, the member 46 can be made of two components (46a, 46b) adhered together, with an internal chamber 46c for accommodating wiring.

Each member 46 is mounted to its carrier member 42 so as to be horizontal with the discs spaced-apart across the tank. In each fish tank the member 46 of one electrode is mounted towards the bottom of the tank with its discs facing upwards whilst the other member 46 is mounted towards the water surface with its discs facing downwards: in this manner the pair of electrodes will pick-up the vertical component of the electrical potentials generated in response to fish activity, the vertical component being dominant.

A third electrode 50 is hung from one side of each fish tank, this electrode comprising three discs encapsulated in a PVC member just as the electrodes 40. This electrode 50 serves as a reference electrode and is movable along the tank to obtain the optimum position.

The above-described disposition of the pair of electrodes, to pick up the vertical component of the electrical potentials, is usually necessary if the outlets of the fish tanks do not have any means (such as tubing 110) to reduce cross-talk. However, if such means are provided, then the pair of the electrodes need not be disposed as described but can instead be arranged in the same fashion as reference electrode 50, i.e. hooked over the wall of the tank (one at each end of the tank) with the planes of the discs substantially vertical. Even though in this disposition, the electrodes will pick up the cross-talk (which is horizontal) the amount is too small for it be be significant. FIG. 7 merely shows schematically the hook-shape of such an electrode.

It will be appreciated that the arrangement of tanks provides for ease of maintenance. The electrodes and baffle member can readily be lifted from the individual fish tanks and the fish tanks can readily be lifted from the main tank for cleaning purposes or for replacing the fish.

The electrical signal generated by the fish is small: a source of noise is the varying impedance path to ground via the running inlet and oulet water. It will be noted however, that in the arrangement shown, the water enters under constant conditions and the final water outlet (over the weir 32) is situated a considerable distance from the various pairs of electrodes.

The monitoring apparatus further comprises a micro computer system for monitoring and analysing the electrical output from the pair of electrodes at the opposite ends of each fish tank. This system monitors a small oscillating voltage which is produced by the fish in ventilation: an appropriate species of fish is rainbow trout. For such trout 15 cm in length, the amplitude of this voltage, as detected by the electrodes, is of the order of 40 to 100 $\mu v$. A rise in ventilation frequency or an increase in the frequency of abnormal behaviour such as "coughing" is indicative of the contaminated water.

The monitoring apparatus thus amplifies the detected voltage from each fish tank which is then subjected to analogue to digital conversion. The micro computer then carries out a Fourier Transform to derive a power spectrum in which the ventilation frequency is identified as a peak which is easily distinguishable from a peak due to mains hum The power spectrum is accordingly scanned over an expected range of fish ventilation frequencies, typically 0.3 to 3 Hz, to detect a peak of greater than a selected threshold and thus establish the ventilation frequency. In order to detect for significant changes in ventilation frequency, a set of measured ventilation frequencies is compared with a set obtained, say, an hour previously: then the number of newly measured frequencies which lie outside a range defined by, say, the 5% and 95% limits of the older set is used as a measure of change in behaviour of the fish.

Figure 9:
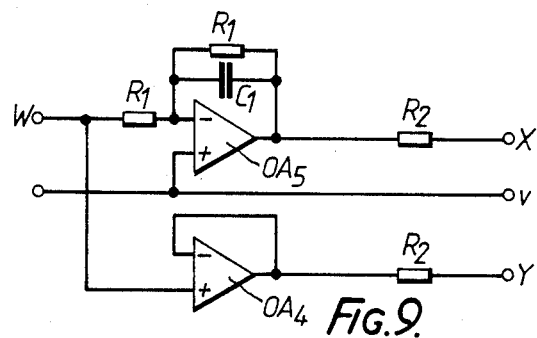
FIG. 9 is a circuit diagram of one form of intermediate stage of the amplifier.
Figure 10:
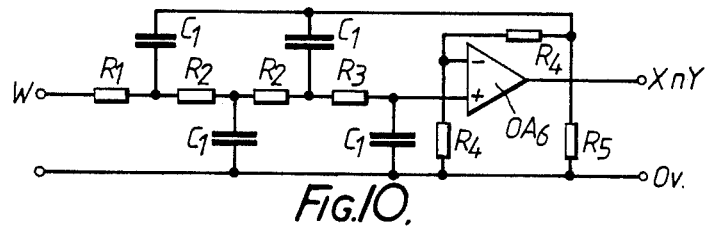
FIG. 10 is a circuit diagram of an alternative form of intermediate stage.
Figure 11:
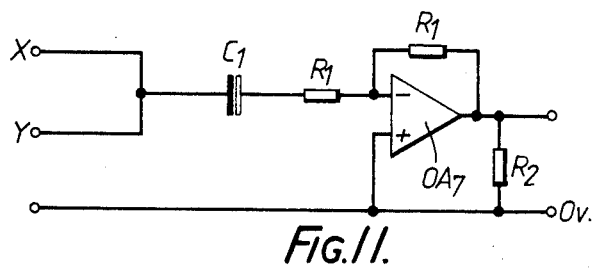
FIG. 11 is a circuit diagram of an output stage of the amplifier.

The amplifier associated with each fish tank is shown in FIGS. 8 to 11, FIG. 8 showing the input stage, FIGS. 9 and 10 alternative intermediate stages and FIG. 11 an output stage. In the input stage (FIG. 8), the paid of electrodes $E_1$, $E_2$ are connected to respective operational amplifiers $OA_1$ and $OA_2$, whose other inputs are connected to a potentiometer P which is connected between their outputs. These outputs are connected through resistances to respective inputs of a third operational amplifier $OA_3$ which provides the output W of the input stage. The third or reference electrode $E_{REF}$ of the fish tank is connected to the Ov rail of the amplifier. Since the "live" electrodes $E_1$ and $E_2$ are not in direct contact with the signal source (the fish), the conductive path by which the signal reaches these electrodes is varying and the input of the amplifier is connected to a source impedance that is unbalanced and changing. The reference electrode, being star connected and eliminating ground loops, leads to a near-balanced source impedance. The potentiometer P serves for calibration to eliminate zero offset.

The intermediate stage shown in FIG. 9 comprises a unity gain amplifier $OA_4$ in parallel with a single stage integrator $OA_5$, these two circuits both receiving the output W of the input stage. The outputs Y and X of these circuits are summed before amplification in the output stage (FIG. 11). The unity gain amplifier thus simply passes to the output stage the output signal from the input stage, whilst the integrator provides an output proportional to the D.C. offset due to the electrode potential: upon summing these signals, the result is to reduce significantly the effect of electrode offset potential on the final signal. Both the input and final stages provide some filtering and overall, with the intermediate stage of FIG. 9, a level passband of 0.5 to 4 Hz is achieved: there is no particularly sharp roll-off characteristic to deal with excessive 50 Hz interference but this can be dealt with in the subsequent digital signal processing.

The alternative intermediate stage shown in FIG. 10 includes a fourth order low-pass Butterworth filter connected to an operational amplifier $OA_6$ and providing a sharp roll-off characteristic to minimise the effect of 50 Hz interference and a level passband from 0.5 to 2.5 Hz.

The final or output stage (FIG. 11) comprises an operational amplifier $OA_7$ to which the output(s) of the intermediate stage are a.c. coupled.

The entire monitoring apparatus (tank arrangement, micro computer system, tanks for fish in stand-by) can be such that it may be installed, for operation, in a mobile vehicle or vehicle trailer so as to be transportable from site-to-site.

Figure 12:
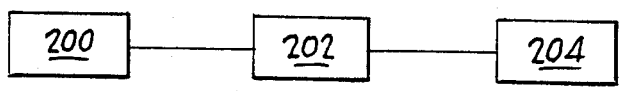
FIG. 12 is a schematic illustration of the overall electrical system employed in carying out the invention.

FIG. 12 schematically illustrates the overall electrical system in carrying out the invention as aforedescribed. In FIG. 12, the electrodes are generally indicated at 200, and are connected to the micro computer system, generally indicated at 202 and including one of the amplifier arrangements of FIGS. 8 to 11, for example. System 202 monitors the signals. And, means generally designated 204 are provided, connected to system 202, for indicating the quality of the water supply in dependence on the monitoring of the signals from the electrodes.

We claim:

1. Apparatus for continuously monitoring the quality of a flowing water supply, which apparatus comprises a main water tank comprising means dividing the tank into a plurality of discrete regions within said tank each for confining an aquatic animal which naturally emits electric signals indicative of its condition; means for dividing the flowing water supply into a series of separate parallel flowing streams and to provide a separate said stream to flow through each said region and out therefrom; in each region a pair of electrodes mounted with respect to said tank and spaced apart to receive electric signals from the aquatic animal within said respective region, each said electrode comprising at least one sintered element of silver and silver chloride encapsulated in insulating material but with a major face of the sintered element exposed at a surface of the electrode; electrical conducting means for conducting said electric signals away from each said electrode pair; an electronic system arranged to receive said signals from said conducting means and to monitor said signals, said system including means for indicating the quality of the water supply in dependence on the said monitoring of the signals.

2. Apparatus according to claim 1, wherein the regions are so arranged as to confine fish.

3. Apparatus according to claim 1, which includes an overflow outlet from said main tank for the water to exit from the main tank.

4. Apparatus according to claim 1, which includes a plurality of animal tanks removably positioned in said main tank, each said animal tank constituting a said discrete region in said main tank.

5. Apparatus according to claim 4, which comprises a header tank for receiving the water supply to be monitored, and wherein said dividing means comprises a piping system for distributing the water into each individual animal tank at one end thereof, each animal tank having a water outlet at its opposite end for the water to flow therefrom into the main tank.

6. Apparatus according to claim 1, wherein each electrode comprises three said sintered elements in the form of discs spaced apart in line and encapsulated in a flat plastics member of insulating material, one side of each disc being coplanar with one side of the flat member.

7. Apparatus for continuously monitoring the quality of a flowing water supply, which comprises a main water tank, a plurality of smaller tanks removably positioned in said main tank, each said smaller tank being arranged to confine a fish therein; each said smaller tank having a pair of electrodes mounted therein, in spaced relationship to receive the electrical signals emitted by the fish in the respective smaller tank, each said electrode comprising at least one sintered element of silver and silver chloride encapsulated in insulating material but with a major face of the sintered element exposed at a surface of the electrode; means for dividing the flowing water supply into a series of parallel flowing streams to provide one said stream through each said smaller tank and out from an outlet thereof into said main tank; means for conducting the electrical signals received by each pair of electrodes to an electronic system comprising means for monitoring said signals, and means for indicating the quality of the flowing water supply in dependence on said monitoring of said signals; and wherein each said outlet is so arranged as to provide additional electrical resistance between the water in that smaller tank and the water which is in the main tank but not in any smaller tank.

8. Apparatus according to claim 7, wherein the said water outlet of each animal tank includes a short tube through which all the water exiting from that animal tank must flow, the bore and length of the tube being such as to provide said additional electrical resistance.

9. Apparatus according to claim 7, wherein each electrode comprises three said sintered elements in the form of discs spaced apart in line and encapsulated in a flat plastics member of insulating material, one side of each disc being coplanar with one side of the flat member.

10. A method of continuously monitoring a flowing water supply, which comprises dividing the supply into a series of parallel flowing streams, and feeding each stream through a respective discrete region of a main water tank, comprising a plurality of said regions, each said region containing a fish, providing a pair of spaced apart electrodes in each said region to receive electric signals naturally emitted by the fish in that region, each said electrode comprising at least one sintered element of silver and silver chloride encapsulated in insulating material but with a major face of the sintered element exposed at a surface of the electrode, conducting the electric signals from each electrode pair to an electronic system and using the system to monitor the electric signals from the electrodes in the individual regions and therefrom to indicate the quality of the flowing water supply.

11. A method according to claim 10, wherein a plurality of fish tanks are located in said main tank, each fish tank constituting a said region and receiving its respective stream of water at one end, and having an outlet at its other end for the water to exit therethrough.

12. A method according to claim 11, which comprises flowing the water exiting from each fish tank through a tube into said main tank, the length and bore of the tube being such as to provide an increased resistance between the water in the fish tank and the water which is in the main tank but not in a fish tank.

* * * * *